US012805741B2

(12) United States Patent

Guan et al.

(10) Patent No.: US 12,805,741 B2
(45) Date of Patent: Nov. 24, 2026

(54) EXCITATION RESPONSE MEASUREMENT METHOD, ELECTRICAL IMPEDANCE TOMOGRAPHY METHOD, AND STORAGE MEDIUM

(71) Applicants: BEIJING HUARUI BOSHI MEDICAL IMAGING TECHNOLOGY CO., LTD., Beijing (CN); TSINGHUA UNIVERSITY, Beijing (CN)

(72) Inventors: Mingtao Guan, Beijing (CN); Xin Zhang, Beijing (CN); Zhichao Lin, Beijing (CN)

(73) Assignees: BEIJING HUARUI BOSHI MEDICAL IMAGING TECHNOLOGY CO., LTD., Beijing (CN); TSINGHUA UNIVERSITY, Beijing (CN)

( * ) Notice: Subject to any disclaimer, the term of this patent is extended or adjusted under 35 U.S.C. 154(b) by 628 days.

(21) Appl. No.: 18/021,713

(22) PCT Filed: Aug. 18, 2021

(86) PCT No.: PCT/CN2021/113157

§ 371 (c)(1),
(2) Date: Feb. 16, 2023

(87) PCT Pub. No.: WO2022/037598

PCT Pub. Date: Feb. 24, 2022

(65) Prior Publication Data

US 2023/0320608 A1 Oct. 12, 2023

(30) Foreign Application Priority Data

Aug. 21, 2020 (CN) ........................ 202010850613.X

(51) Int. Cl.
*A61B 5/0536* (2021.01)
*A61B 5/00* (2006.01)

(52) U.S. Cl.
CPC .......... *A61B 5/0536* (2013.01); *A61B 5/6831* (2013.01)

(58) Field of Classification Search
CPC ................ A61B 5/0536; A61B 5/6831; A61B 2562/0209; A61B 2562/043; A61B 2562/046; A61B 5/7257
See application file for complete search history.

(56) References Cited

U.S. PATENT DOCUMENTS 5,626,146 A 5/1997 Barber et al.
2010/0255795 A1* 10/2010 Rubinsky ............ A61B 5/0536 455/90.1

(Continued)

FOREIGN PATENT DOCUMENTS

CN 103065286 A 4/2013
CN 111343918 A 6/2020

(Continued)

OTHER PUBLICATIONS

Extended European Search Report received in corresponding EP Application No. 21857690.8, dated Aug. 20, 2024, in 7 pages.

(Continued)

*Primary Examiner* — Joanne M Rodden
*Assistant Examiner* — Dana Stumpfoll
(74) *Attorney, Agent, or Firm* — Procopio, Cory, Hargreaves & Savitch LLP

(57) ABSTRACT

An excitation response measurement method, an electrical impedance tomography method, and a storage medium are provided. The excitation response measurement method comprises: respectively applying, at the same moment, excitation currents having different frequencies within a designated frequency range to excitation electrode pairs of at least two electrode belts, and measuring a voltage difference of a measurement electrode pair of each electrode belt at the moment, wherein the excitation electrode pair is selected from multiple electrodes of the same electrode belt, and the measurement electrode pair is selected from electrodes in (Continued)

the same electrode belt other than the excitation electrode pair; and separating the measured voltage differences of the measurement electrode pairs into multiple sets of voltage differences respectively corresponding to the different frequencies of the excitation currents, and using the multiple sets of voltage differences as electrical impedance tomography data.

20 Claims, 6 Drawing Sheets

(56) References Cited

U.S. PATENT DOCUMENTS

| | | | | |
|---|---|---|---|---|
| 2019/0142299 | A1* | 5/2019 | Holzhacker .......... | A61B 5/0536 600/390 |
| 2019/0328277 | A1* | 10/2019 | Woo ..................... | A61B 5/6823 |

FOREIGN PATENT DOCUMENTS

| | | | | |
|---|---|---|---|---|
| EP | 3 542 706 | A1 | 9/2019 | |
| JP | 2020-503989 | A | 2/2020 | |
| WO | 2010/126827 | A2 | 11/2010 | |
| WO | WO-2020128079 | A1 * | 6/2020 | ............ A61M 25/09 |

OTHER PUBLICATIONS

Notification of Reasons for Refusal received in corresponding JP Application No. 2023-512478, dated Apr. 9, 2024, in 8 pages, with translation.

International Search Report received in International Patent Application No. PCT/CN2021/113157, mailed Nov. 18, 2021, in 4 pages.

* cited by examiner

EXCITATION RESPONSE MEASUREMENT METHOD, ELECTRICAL IMPEDANCE TOMOGRAPHY METHOD, AND STORAGE MEDIUM

CROSS REFERENCE TO RELATED APPLICATIONS

The present application is a 371 national stage application of International Patent Application No. PCT/CN2021/113157, filed, Aug. 18, 2021, which claims the priority of the Chinese Patent Application No. CN202010850613.X, entitled "Excitation Response Measurement Method, Electrical Impedance Tomography Method, and Storage Medium", filed on Aug. 21, 2020, which is herein incorporated by reference in its entirety.

FIELD OF THE INVENTION

The present disclosure relates to a technical field of biomedical electrical impedance tomography, and in particular to an excitation response measurement method, an electrical impedance tomography method and a storage medium.

BACKGROUND OF THE INVENTION

Electrical Impedance Tomography (EIT) is a non-invasive biomedical imaging technology utilizing the electrical impedance characteristics of a measured organism to image. It reconstructs an electrical impedance distribution map inside the organism by applying safe currents to the surface of the organism and measuring surface voltages. As the electrical impedance characteristics differ considerably in various tissues and organs of a human body and also change in the same tissue for different states, the reconstructed image through the electrical impedance tomography technology has relative high contrast, and the measured organism can be monitored for a long time. The biomedical electrical impedance tomography has advantages of high resolution, low cost, equipment portability, no radiation and real-time monitoring, thus it has a wide range of applications.

When the three-dimensional electrical impedance tomography is performed on human bodies, excitation currents conduct not only in the measurement plane, but also in the three-dimensional space. Therefore, it is necessary to arrange several electrode belts at equal intervals around an imaged part (such as the chest), with the same number of electrodes evenly or unevenly distributed on each electrode belt. In order to obtain measurement data needed for three-dimensional electrical impedance image reconstruction, a sequential excitation-measurement method is usually adopted at present. Taking two electrode belts as an example (as shown in FIG. 1), they can be divided into an upper electrode belt 1 and a lower electrode belt 2 based on different wearing positions. Each electrode belt has 16 electrodes. For example, the selection of an excitation electrode pair and a measurement electrode pair is based on an adjacent-electrode method. Specifically, excitation currents are firstly applied to the electrode 11 and the electrode 12 of the upper electrode belt 1 to establish a quasi-steady state current field, and the voltage differences between the electrode 13 and the electrode 14 of the electrode belt 1 and between the electrode 23 and the electrode 24 of the lower electrode belt 2 are then simultaneously measured. With the excitation currents unchanged, the corresponding measurement electrode pairs on the upper and lower electrode belts are measured clockwise through the same method until the measurement electrode pairs turn to the electrode 116 and the electrode 115 on the electrode belt 1, and the electrode 216 and the electrode 215 on the electrode belt 2, and a set of measurement data is obtained for the case that the electrodes 11 and 12 are excited. Next, an adjacent electrode pair on the electrode belt 1 is selected clockwise as excitation electrodes, and the above operations are repeated until the excitation electrode pair becomes the electrodes 11 and 116, and the measurement data of the upper and lower electrode belts are obtained when the upper electrode belt is excited. The same method is adopted to excite electrode pairs on the lower electrode belt 2. Finally, four sets of data are obtained, namely, the measurement data of the upper electrode belt when the upper electrode belt is excited, the measurement data of the lower electrode belt when the upper electrode belt is excited, the measurement data of the upper electrode belt when the lower electrode belt is excited, and the measurement data of the lower electrode belt when the lower electrode belt is excited. For this method, the selection of excitation electrode pairs and measurement electrode pairs is not limited to the adjacent-electrode method, and it is easy to be extended to the case of multiple electrode belts.

However, the conventional sequential excitation-measurement method described above cannot meet real-time measurement requirements of the three-dimensional electrical impedance tomography due to single excitation and the resulting long time in the measurement process.

SUMMARY OF THE INVENTION

The technical problem to be solved by the present disclosure is that single excitation in the measurement process is adopted in the conventional sequential excitation-measurement method, which takes a long time and cannot meet real-time measurement requirements of the three-dimensional electrical impedance tomography.

To solve the above problem, an excitation response measurement method, an electrical impedance tomography method, and a storage medium is provided in the present disclosure.

In the first aspect, a method for measuring excitation response is provided in the present disclosure. The method is applied to an electrical impedance tomography device. The electrical impedance tomography device comprises at least two electrode belts and each electrode belt comprises multiple electrodes.

In the excitation response measurement method, excitation currents having different frequencies within a designated frequency range are applied at the same moment to excitation electrode pairs of at least two electrode belts respectively, and a voltage difference of a measurement electrode pair of each electrode belt at the moment is measured. The excitation electrode pair is selected from multiple electrodes of the same electrode belt, and the measurement electrode pair is selected from electrodes in the same electrode belt other than the excitation electrode pair. The measured voltage differences of the measurement electrode pairs are separated into multiple sets of voltage differences respectively corresponding to the different frequencies of the excitation currents, and the multiple sets of voltage differences are used as electrical impedance tomography data.

Preferably, a quotient value obtained by dividing a difference value between an upper limit value and a lower limit value of the designated frequency range by the lower limit value does not exceed 20%.

Preferably, the step of applying, at the same moment, excitation currents having different frequencies within the designated frequency range to excitation electrode pairs of at least two electrode belts respectively, and measuring a voltage difference of a measurement electrode pair of each electrode belt at the moment, further comprises the following three steps:

step one, respectively selecting, from each electrode belt, an excitation electrode pair and a corresponding measurement electrode pair;

step two, respectively applying, at the same moment, excitation currents having different frequencies within the designated frequency range to the excitation electrode pairs of all the electrode belts, and measuring voltage differences of all the measurement electrode pairs at the moment to obtain the voltage differences of all the measurement electrode pairs; and step three, selecting, from multiple electrodes of each electrode belt, an excitation electrode pair and a corresponding measurement electrode pair for multiple times according to the step one, and then measuring the excitation electrode pair and its corresponding measurement electrode pair selected each time according to step two until the selection of the excitation electrode pair on each electrode belt traverses all the electrodes on the electrode belt, wherein the excitation electrode pair selected each time is different from each other.

Preferably, the step of respectively selecting, from each electrode belt, an excitation electrode pair and a corresponding measurement electrode pair, further comprises the following steps: respectively selecting, from each electrode belt, an excitation electrode pair; and for each selected excitation electrode pair, dividing the electrodes, other than the excitation electrode pair, in multiple electrodes of the electrode belt to which the excitation electrode pair belongs, into multiple measurement electrode pairs as the corresponding measurement electrode pairs.

Preferably, an excitation electrode pair is selected from each electrode belt according to any one of an adjacent-electrode method, an opposite-electrode method and an interdigitated-electrode method.

Preferably, the electrodes, other than the excitation electrode pair, in multiple electrodes of the electrode belt to which the excitation electrode pair belongs, are divided into multiple measurement electrode pairs, according to any one of the adjacent-electrode method, the opposite-electrode method and the interdigitated-electrode method.

Preferably, the excitation electrode pairs excited at the same moment on different electrode belts are distributed in up-and-down correspondence at spatial positions around an area to be measured.

Preferably, the step of separating the measured voltage differences of the measurement electrode pairs into multiple sets of voltage differences respectively corresponding to the different frequencies of the excitation currents, further comprises the following steps: performing discrete Fourier transform on the voltage differences of the measurement electrode pairs to obtain frequency-domain signals corresponding to the voltage differences; sequentially taking, according to excitation frequencies of different electrode belts, a midpoint value of each two adjacent excitation frequencies as a boundary frequency of the frequency-domain signals; separating, according to the boundary frequency, the frequency-domain signals corresponding to the voltage differences; and performing inverse discrete Fourier transform on the separated frequency-domain signals to obtain multiple sets of voltage differences respectively corresponding to the different frequencies.

In the second aspect, an electrical impedance tomography method is provided in the present disclosure, which comprises the following steps: obtaining electrical impedance tomography data by the method for measuring excitation response described above; and reconstructing an electrical impedance image in an area to be measured according to the electrical impedance tomography data.

In the third aspect, a storage medium is provided in the present disclosure, on which a computer program for realizing the steps of the above method for measuring excitation response or realizing the steps of the above electrical impedance tomography method is stored.

In the application of the method for measuring excitation response according to the present disclosure, excitation currents having different frequencies within the designated frequency range are applied at the same moment to excitation electrode pairs of at least two electrode belts respectively, and a voltage difference of a measurement electrode pair of each electrode belt at the moment is measured. The excitation electrode pair is selected from multiple electrodes of the same electrode belt, and the measurement electrode pair is selected from electrodes in the same electrode belt other than the excitation electrode pair. The measured voltage differences of the measurement electrode pairs are separated into multiple sets of voltage differences respectively corresponding to the different frequencies of the excitation currents, and the voltage differences are used as electrical impedance tomography data. Thus, on the premise of satisfying the real-time measurement of three-dimensional impedance tomography, faster data acquisition speed than that of the conventional sequential excitation-measurement method is achieved.

Other features and advantages of the present disclosure will be set forth in the subsequent specification, and will become apparent in part from the specification, or will be understood through the implementation of the present disclosure. The objects and other advantages of the present disclosure can be realized and obtained by the specification, the claims and the structures specially pointed out in the drawings.

BRIEF DESCRIPTION OF THE DRAWINGS

The drawings are used to provide a further understanding of the disclosure and form a part of the specification. They are used together with the examples of the disclosure to explain the disclosure, and do not constitute restrictions on the disclosure. In the accompanying drawing.

LIST OF THE DRAWING REFERENCE SIGNS

1 Upper electrode belt
2 Lower electrode belt
11-116 Electrodes in the upper electrode belt
21-216 Electrodes in the lower electrode belt
3 Current line
4 Equal potential

DETAILED DESCRIPTION OF THE EMBODIMENTS

The embodiments of the present disclosure will be described in detail below in combination with the Drawings and Examples, so as to fully understand and implement the realization process of how the disclosure applies technical means to solve technical problems and achieve technical effects. It should be noted that, all the Examples and all the features therein of this disclosure can be combined with each other as long as they do not constitute conflicts, and the resulting technical solutions are within the protection scope of this disclosure.

Example 1

In order to solve the above technical problem in the prior art, this example of the present disclosure provides a method for measuring excitation response.

Figure 2:
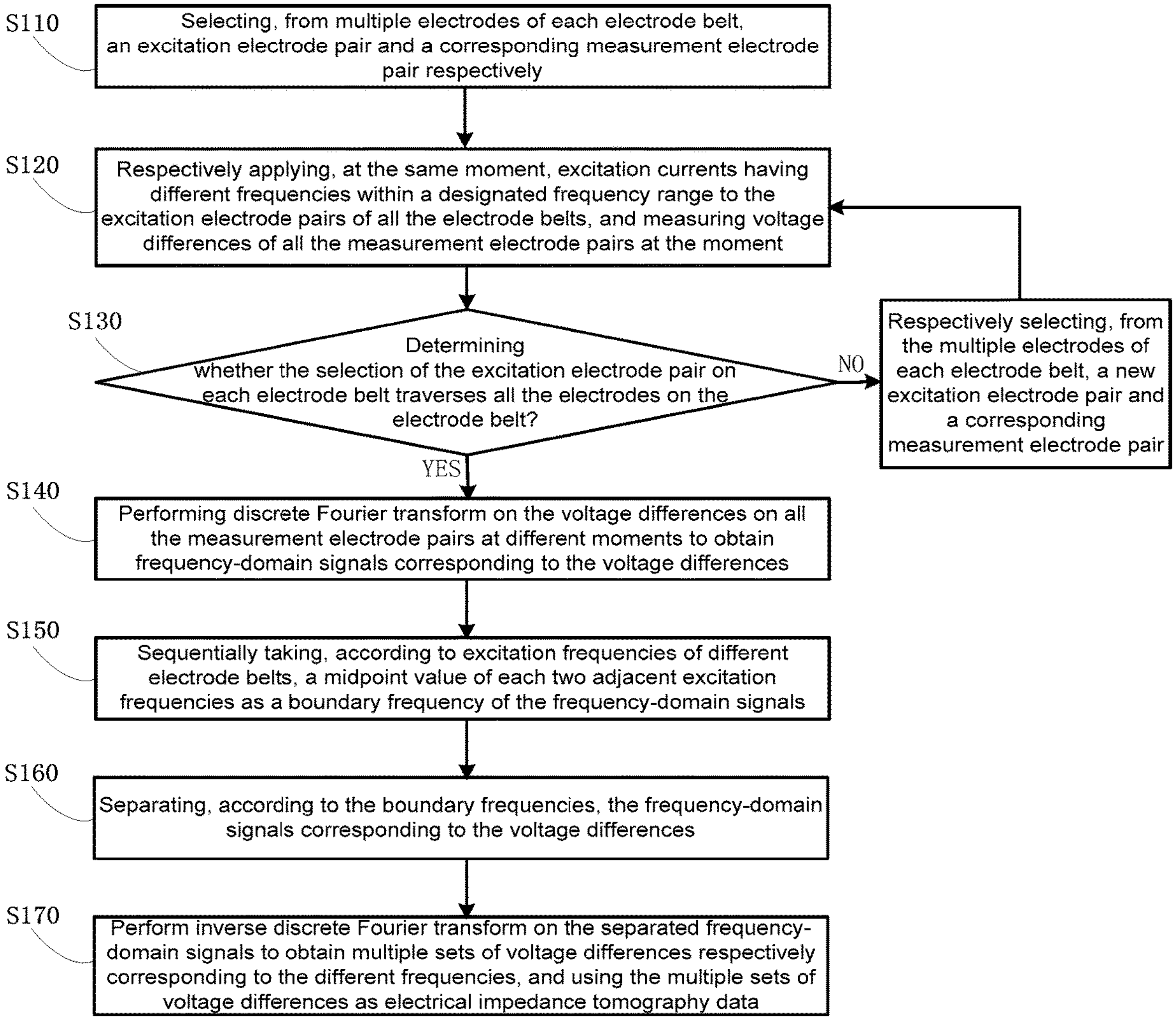
FIG. 2 shows a flow chart of a method for measuring excitation response according to Example 1 of the present disclosure.

With reference to FIG. 2, the method for measuring excitation response according to this example can be applied to an electrical impedance tomography device, which comprises at least two electrode belts, and each electrode belt comprises multiple electrodes. The method comprises the following steps S110 to S170:

S110, respectively selecting, from multiple electrodes of each electrode belt, an excitation electrode pair and a measurement electrode pair corresponding to the excitation electrode pair;

S120, respectively applying, at the same moment, excitation currents having different frequencies within a designated frequency range to the excitation electrode pairs of all the electrode belts, and measuring voltage differences of all the measurement electrode pairs at the same moment to obtain the voltage differences of all the measurement electrode pairs;

S130, determining whether the selection of the excitation electrode pair on each electrode belt traverses all the electrodes on the electrode belt: if yes, performing step S140; if not, selecting, from multiple electrodes of each electrode belt, a new excitation electrode pair and a corresponding measurement electrode pair, and returning to step S120;

S140, performing discrete Fourier transform on the voltage differences of all the measurement electrode pairs at different moments to obtain frequency-domain signals corresponding to the voltage differences;

S150, sequentially taking, according to excitation frequencies of different electrode belts, a midpoint value of each two adjacent excitation frequencies as a boundary frequency of the frequency-domain signals;

S160, separating, according to the boundary frequency, the frequency-domain signals corresponding to the voltage differences; and

S170, performing inverse discrete Fourier transform on the separated frequency-domain signals to obtain multiple sets of voltage differences respectively corresponding to different frequencies, and using the multiple sets of voltage differences as electrical impedance tomography data.

In step S110, a quotient value obtained by dividing a difference value between an upper limit value and a lower limit value of the designated frequency range by the lower limit value does not exceed 20%.

In step S110, the excitation electrode pairs excited at the same moment on different electrode belts are distributed in up-and-down correspondence at spatial positions around an area to be measured.

In the method for measuring excitation response according to this example, excitation currents having different frequencies within the designated frequency range are applied to the excitation electrode pairs of all the electrode belts at the same moment. In other words, several excitation currents having similar but different frequencies are used to excite each electrode belt at the same moment, and each electrode belt corresponds to an excitation current with one frequency. Compared with the conventional sequential excitation-measurement method, where one electrode belt is excited at a time, all the electrode belts are simultaneously excited in the method of this example, so that the excitation efficiency is improved. The voltage differences of all the measurement electrode pairs are measured at the same moment of excitation, that is, in each measurement, not only multiple electrode belts are excited at the same moment but also the electrodes on the multiple electrode belts are measured at the same moment, so as to improve the measurement efficiency.

In the method for measuring excitation response according to this example, the discrete Fourier transform is used to transform the measurement data into the frequency-domain signals, the frequency-domain signals are separated according to the different excitation frequencies, and the inverse discrete Fourier transform is then performed to obtain the measurement data of each electrode belt during single frequency excitation of the conventional sequential excitation-measurement method. Therefore, the method for measuring excitation response according to this example can ensure the same measurement data as that of the conventional sequential excitation-measurement method, and greatly improve the efficiency of measurement data.

Example 2

In order to solve the above technical problem in the prior art, this example of the present disclosure provides a method for measuring excitation response based on Example 1, and improves step S110 in Example 1.

Figure 3:
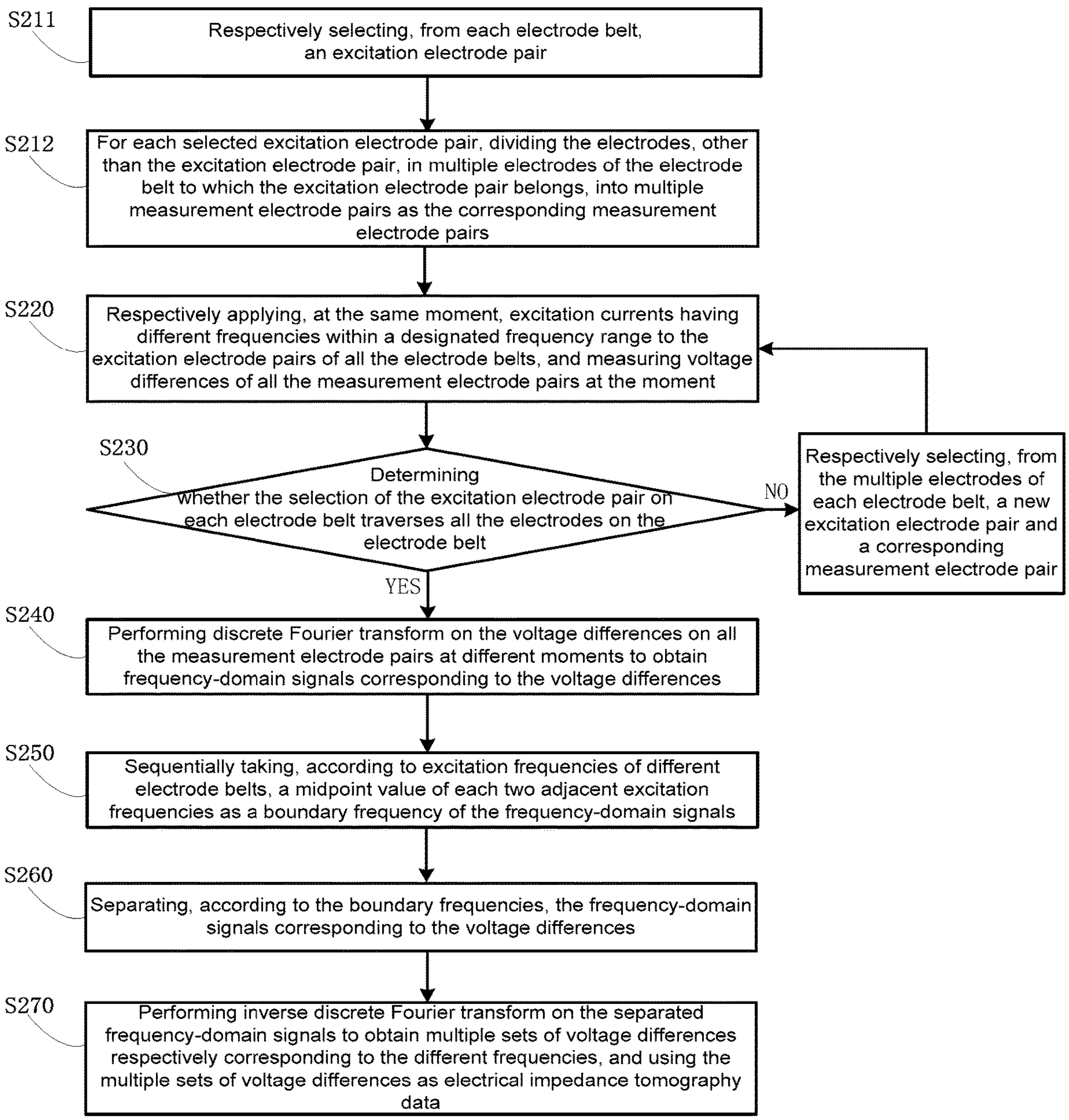
FIG. 3 shows a flow chart of a method for measuring excitation response according to Example 2 of the present disclosure.

With reference to FIG. 3, the method for measuring excitation response according to this example comprises the following steps S211 to S270:

S211, selecting, from each electrode belt, an excitation electrode pair;

S212, for each selected excitation electrode pair, dividing the electrodes, other than the excitation electrode pair, in multiple electrodes of the electrode belt to which the excitation electrode pair belongs, into multiple measurement electrode pairs as the measurement electrode pairs corresponding to the excitation electrode pair;

S220, respectively applying, at the same moment, excitation currents having different frequencies within a designated frequency range to excitation electrode pairs of all the electrode belts, and measuring voltage differences of all the measurement electrode pairs at the same moment to obtain the voltage differences of all the measurement electrode pairs;

S230, determining whether the selection of the excitation electrode pair on each electrode belt traverses all the electrodes on the electrode belt: if yes, performing step S240; if not, selecting, from multiple electrodes of each electrode belt, a new excitation electrode pair and corresponding measurement electrode pairs, and returning to step S220;

S240, performing discrete Fourier transform on the voltage differences of all the measurement electrode pairs at different moments to obtain frequency-domain signals corresponding to the voltage differences;

S250, sequentially taking, according to excitation frequencies of different electrode belts, a midpoint value of each two adjacent excitation frequencies as a boundary frequency of the frequency-domain signals;

S260, separating, according to the boundary frequency, the frequency-domain signals corresponding to the voltage differences; and S270, performing inverse discrete Fourier transform on the separated frequency-domain signals to obtain multiple sets of voltage differences respectively corresponding to different frequencies, and using the multiple sets of voltage differences as electrical impedance tomography data.

In step S211, an excitation electrode pair is selected from each electrode belt according to any one of an adjacent-electrode method, an opposite-electrode method and an interdigitated-electrode method.

In step S212, the electrodes, other than the excitation electrode pair, in multiple electrodes of the electrode belt to which the excitation electrode pair belongs, are divided into multiple measurement electrode pairs, according to any one of the adjacent-electrode method, the opposite-electrode method and the interdigitated-electrode method.

Example 3

In order to solve the above technical problem in the prior art, the method for measuring excitation response provided in Example 2 is applied to the scene of three-dimensional electrical impedance tomography of human bodies in this example of the present disclosure.

The method for measuring excitation response according to this example comprises two steps, namely, data acquisition and frequency-domain separation.

Specifically, when the three-dimensional electrical impedance tomography is conducted on human bodies, several electrode belts (such as 2 belts) are distributed at equal intervals around the part to be measured (such as the chest), with the same number of electrodes (such as 16 electrodes) evenly or unevenly distributed on each electrode belt. In the data acquisition stage, excitation currents, with the number equal to that of electrode belts and having similar but different frequencies, are respectively applied to an excitation electrode pair of each electrode belt, and the spatial positions of excitation electrode pairs on the electrode belts are in up-and-down correspondence. Then, the voltage differences on all the electrode pairs, other than the excitation electrode pair, on each electrode belt are measured clockwise or counterclockwise with a certain rule at the same moment, so as to obtain the measurement data of each electrode belt when an electrode pair is excited. Then, other electrode pairs on the electrode belt are sequentially selected clockwise or counterclockwise with a certain rule as the excitation electrodes. The above steps are repeated until all electrode pairs meeting the rule have been used as the excitement electrode pair, so as to obtain the measurement data of each electrode belt under simultaneous multi-frequency excitation. In the above steps, the selection rules of the excitation electrode pair and the measurement electrode pair comprise but are not limited to the adjacent-electrode method, the opposite-electrode method and the interdigitated-electrode method.

Human bodies can be regarded as a linear system, whose response to the excitation meets the homogeneity, when the three-dimensional electrical impedance tomography is performed on their relevant parts. Therefore, the data measured on each electrode belt in the above data acquisition stage is the result of the combined action of all excitation currents, that is, the measured data of each electrode belt is the sum of the measured signals having several frequencies. Thus, in the frequency-domain separation stage, discrete Fourier transform is first performed on the measured data of each electrode belt to obtain its corresponding frequency spectrum. Then, according to the preset excitation frequency, a midpoint value of each two adjacent frequencies is sequentially taken as a boundary frequency of frequency-domain signals. Then, the frequency-domain signals having different frequencies are separated according to the boundary frequency. Finally, the inverse discrete Fourier transform is performed on the separated frequency-domain signals to obtain the measured data of each electrode belt under single frequency excitation. In the above steps, n sets of data measured on n electrode belts are separated into n^2 sets of data, and the amount of data is the same as that obtained by the sequential excitation-measurement method using single excitation. Since the frequency of each excitation current used in this method is similar, it can be approximately considered that the impedance of the measured parts does not change with the frequency, such that the data obtained by this method are equivalent to the measurement data obtained by the sequential excitation-measurement method using single excitation.

Compared with the sequential excitation-measurement method using single excitation, on the premise of the same data amount obtained, the method for measuring excitation response provided in this example can increase the measurement speed by n times when n electrode belts are used.

Figure 1:
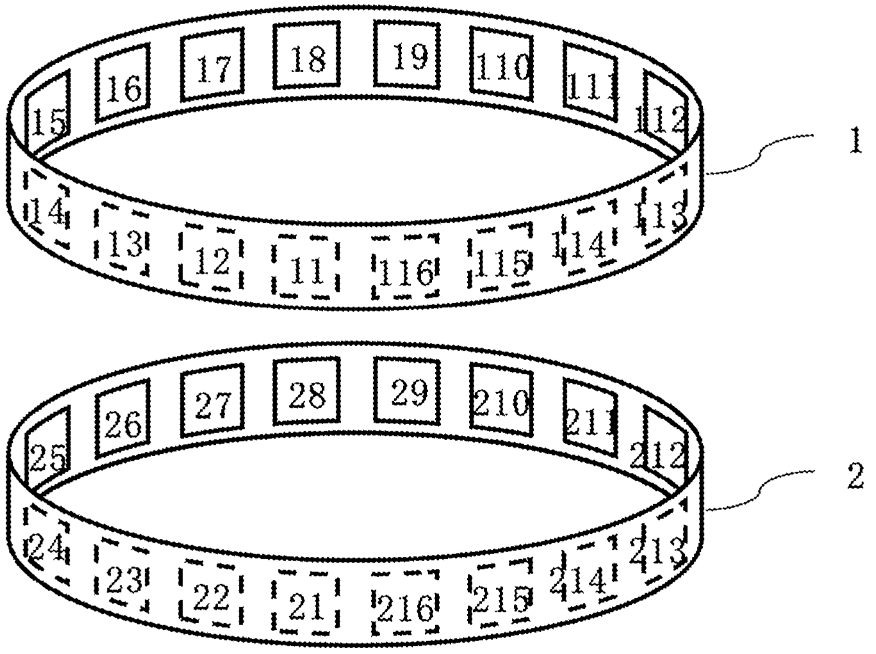
FIG. 1 is a schematic diagram of an electrode belt layout during a three-dimensional electrical impedance tomography.
Figure 4:
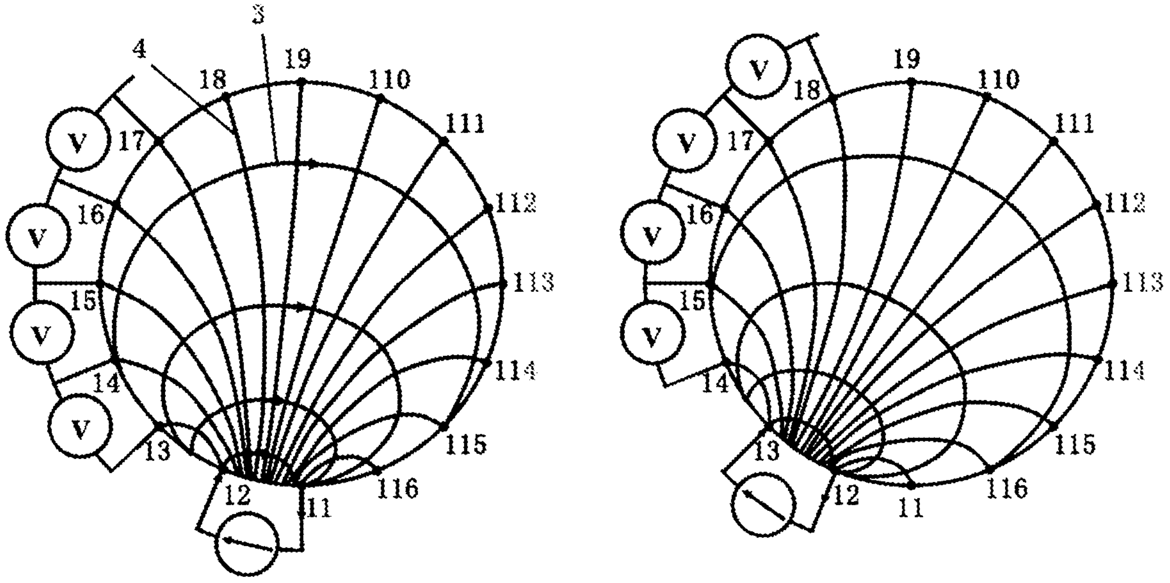
FIG. 4 shows a schematic diagram of a selection method in the electrode belt 1 according to an adjacent-electrode method in Example 3 of the present disclosure.

The method for measuring excitation response according to this example is explained in more detail by the following embodiment. In this embodiment, an electrical impedance tomography device comprises two electrode belts, and each one comprises 16 electrodes. Based on different spatial positions, the two electrode belts can be divided into the upper electrode belt 1 and the lower electrode belt 2 (as shown in FIG. 1). During excitation, 10 kHz and 12 kHz excitation currents are used to excite and measure the two electrode belts, respectively. The adjacent-electrode method is used to select the excitation electrode pairs and the measurement electrode pairs, as shown in FIG. 4.

In the data acquisition stage, a 10 kHz excitation current is applied to the electrode 11 and the electrode 12 of the electrode belt 1, and a 12 kHz excitation current is applied to the electrode 21 and the electrode 22 of the electrode belt 2 at the same moment to establish a quasi-steady state current field. Then, the voltage differences between the electrode 13 and the electrode 14 of the electrode belt 1 and between the electrode 23 and the electrode 24 of the electrode belt 2 are simultaneously measured. The voltage differences between adjacent electrode pairs other than the excitation electrode pairs on the two electrode belts are sequentially measured clockwise, until the measurement electrode pairs turn to the electrodes 115 and 116 of the electrode belt 1, and the electrodes 215 and 216 of the electrode belt 2. Thus, the measurement data when an electrode pair is excited is obtained. Then, the next adjacent electrode pair is selected along a clockwise direction as the excitation electrodes, namely, the electrode 12 and the electrode 13 as well as the electrode 22 and the electrode 23, and the voltage differences of the remaining electrode pairs are measured. The above operation is repeated until all adjacent electrode pairs have been used as excitation electrode pairs for measurement. Finally, a set of measurement data under simultaneous dual-frequency excitation can be obtained for each electrode belt.

Figure 5:
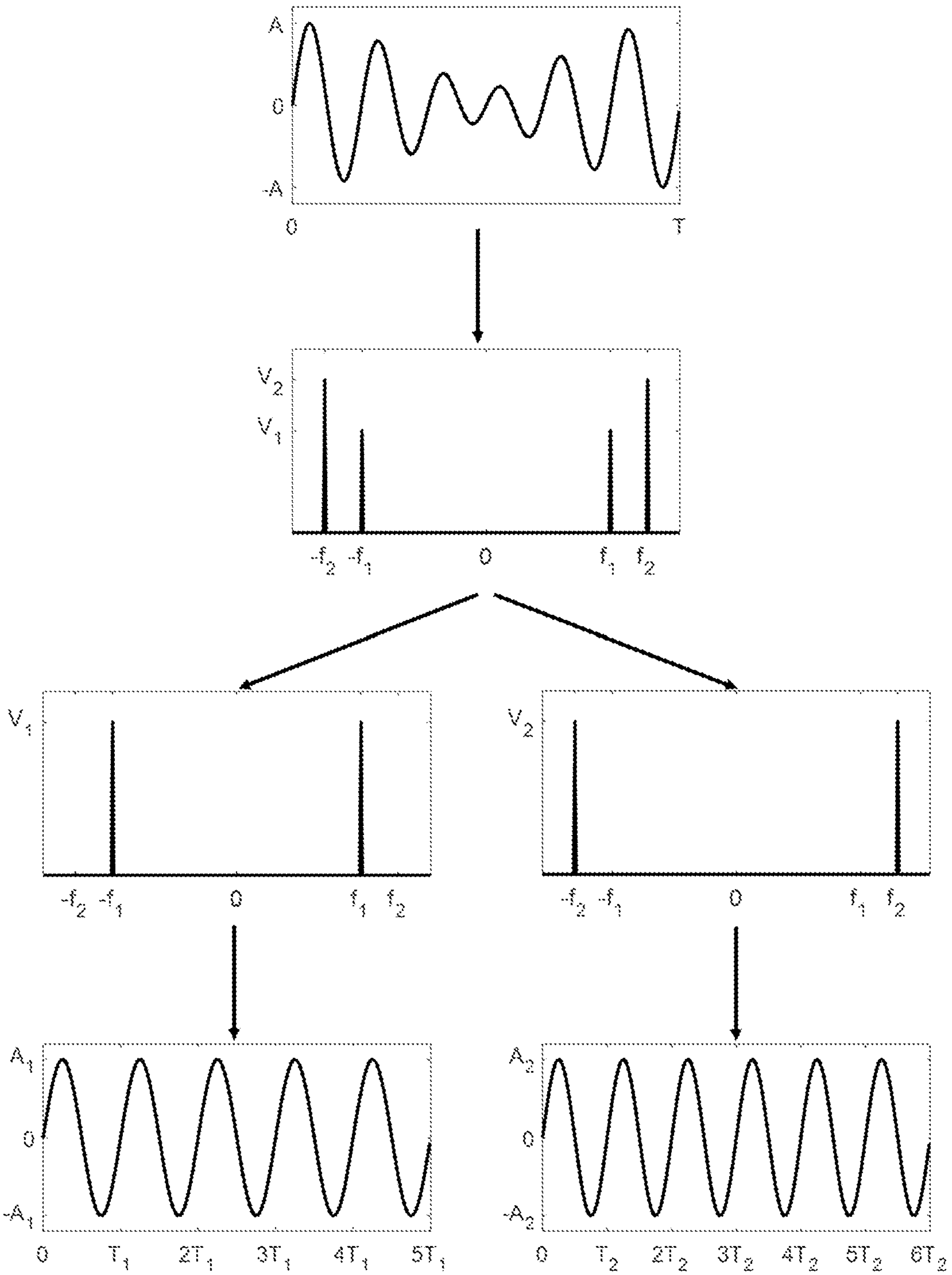
FIG. 5 shows a flow diagram of a frequency-domain separation in Example 3 of the present disclosure.

In the frequency-domain separation stage, the discrete Fourier transform is performed on the two sets of measurement data respectively to obtain the corresponding frequency-domain signals. With 11 kHz taken as a separation frequency, two frequency signals are separated in the frequency-domain. Finally, the inverse discrete Fourier transform is performed on the separated frequency-domain signals to obtain the measurement data under single frequency excitation. FIG. 5 shows a flow diagram of frequency-domain separation. It can be seen that the measurement data of each electrode belt can be separated into two sets of measurement data under single frequency excitation, that is, four sets of measurement data are finally obtained, namely, the measurement data of the upper electrode belt when the upper electrode belt is excited, the measurement data of the upper electrode belt when the lower electrode belt is excited, the measurement data of the lower electrode belt when the lower electrode belt is excited, and the measurement data of the lower electrode belt when the upper electrode belt is excited.

The method for measuring excitation response according to this example overcomes the time-consuming defect of the conventional sequential excitation-measurement method, and is the one that can quickly excite and measure the target to be measured. This method can obtain the same amount of measurement data as that of the conventional sequential excitation-measurement method, and can significantly improve the measurement speed, so as to meet the requirements of real-time tomography.

In practical application, in addition to the adjacent-electrode method, the opposite-electrode method or the interdigitated-electrode method can be used to select an excitation electrode pair and a measurement electrode pair.

Specifically, it is taken into account in the adjacent-electrode method that impedance differences in all directions in the tomographic plane are relatively small. To simplify the calculation, it can be assumed that the impedance is isotropic, so the internal information reflected remains the same when the excitation-measurement electrode pairs are interchanged. For example, the information obtained by measuring the voltage between the electrodes 3 and 4 under the excitation of the electrodes 1 and 2 is equivalent to that obtained by measuring the voltage between the electrodes 1 and 2 under the excitation of the electrodes 3 and 4, therefore, the measurement will not be repeated. For an N-electrode EIT system, a total of "$N\times(N-3)$" boundary voltages can be collected. According to the reciprocity principle, the actual number of independent measurements is "$M=N\times(N-3)/2$".

Figure 6:
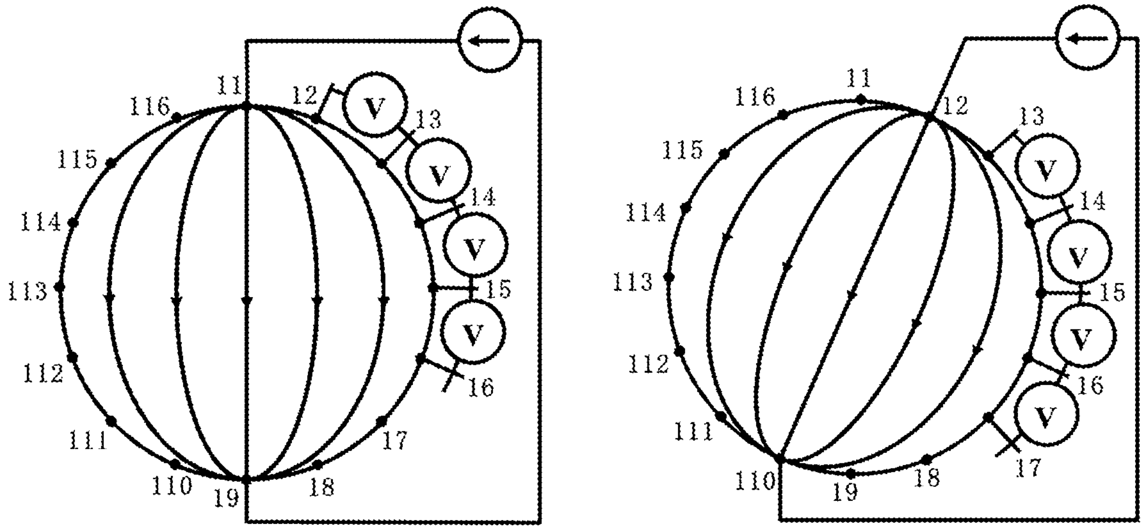
FIG. 6 shows a schematic diagram of a selection method in electrode belts according to a first opposite-electrode method in Example 3 of the present disclosure.
Figure 7:
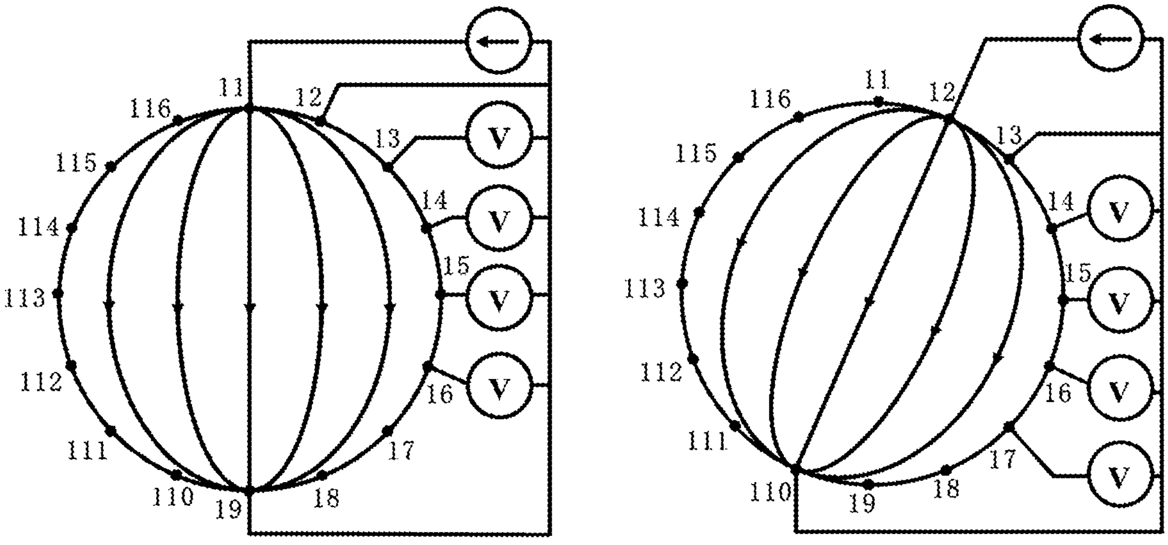
FIG. 7 shows a schematic diagram of a selection method in electrode belts according to a second opposite-electrode method in Example 3 of the present disclosure.

Generally speaking, there are two kinds of opposite-electrode methods. The first one is as follows: excitation currents are injected through two radially opposite electrodes to establish a sensitivity field, and the voltages of other adjacent electrode pairs are measured in turn; then, the next opposite electrode pair is turned to for excitation, and the voltages of other adjacent, non-excitation electrode pairs are measured. The above process is repeated until all adjacent electrode pairs rotate for one turn, as shown in FIG. 6. The actual number of independent measurements is "$M=N\times(3N/2-1)/4$" when the adjacent data acquisition mode is adopted. The second one is as follows: excitation currents are injected through any two radially opposite electrodes, and one electrode adjacent to the excitation electrode pair is used as the voltage reference to measure the voltages of other electrodes other than the excitation electrodes, as shown in FIG. 7. For an N-electrode system, the number of independent measurements in this mode is "$M=N\times(N-3)/2$".

The interdigitated-electrode method is as follows: excitation currents are injected through two relatively distant electrodes to obtain a more uniform current distribution; one electrode adjacent to the excitation electrode pair is used as the voltage reference to measure the voltages of other electrodes other than the excitation electrodes. Taking a 16-electrode system as an example, first, the electrodes 1 and 2 are selected for the reference of excitation currents and measurement voltages, and the electrode 3 is used as an excitation electrode to measure the voltages of other electrodes relative to the electrode 2, and 13 measured values are obtained. Then, the electrodes 5, 7, 9, 11, 13 and 15 are taken as excitation electrodes, the voltages of other electrodes relative to the electrode 2 are measured respectively, and "$13\times7=91$" measured values are obtained in total. Then the electrodes 4 and 3 are selected respectively for the reference of excitation currents and measurement voltages, and the electrode 6 is used as the excitation electrode to measure the voltages of other electrodes relative to the electrode 3, and 13 measured values are obtained. Then, the electrodes 8, 10, 12, 14, 16 and 2 are taken as excitation electrodes respectively, to measure the voltages of other electrodes relative to the electrode 3, and "$13\times7=91$" measured values are further obtained. Only 104 of the 182 measured values are independent of each other.

As the hardware system and the measurement method are relatively simple, the adjacent electrode excitation and opposite electrode excitation modes become the most commonly used methods. More measurement data can be obtained by the adjacent-electrode method, but currents are mainly concentrated near electrodes, and the current is distributed and concentrated on one side of the excitation electrodes. The more electrodes there are, the more obvious this situation is. When the opposite-electrode excitation is used, it can be seen from the equipotential line distribution map that due to the geometric symmetry of the model, the equipotential lines will overlap, only half as much as those of the adjacent electrode excitation, thereby greatly reducing the tomographic resolution. The interdigitated-electrode method, having slightly complicated electrode conversion, is less sensitive than the adjacent electrode at the edge of a tomographic target, but is more sensitive in the whole area.

In fact, in addition to an adjacent-electrode excitation mode, an opposite-electrode excitation mode and an interdigitated-electrode excitation mode, there are many excitation measurement methods, such as an adaptive method, a two-electrode method, a diagonal mode, a conduction boundary mode, a multiple reference mode, a linear array mode, etc.

Example 4

In order to solve the above technical problem in the prior art, this example of the present disclosure further provides an electrical impedance tomography method.

In the electrical impedance tomography method of this example, the electrical impedance tomography data are obtained according to the above method for measuring excitation response; and an electrical impedance image in an area to be measured is reconstructed according to the electrical impedance tomography data.

The electrical impedance tomography data of this example are obtained by exciting and measuring different cross sections of a measured object through multiple electrode belts of the electrical impedance tomography device. The excitement and measurement comprise two stages: data acquisition and data processing. In the data acquisition stage, the electrical impedance tomography device simultaneously applies excitation currents on the electrode pairs at the corresponding positions of each electrode belt to establish a quasi-steady state current field, the frequencies of the excitation currents applied on different electrode belts are similar but different. At the same moment, the voltage differences of other electrode pairs on each electrode belt are measured sequentially and recorded. In the data processing stage, the discrete Fourier transform is performed on the data collected on each electrode belt respectively, and the signals are separated in the frequency-domain, thereby obtaining the same amount of measurement data as that of the conventional sequential excitation-measurement method using single excitation. Compared with the conventional excitation measurement method, this method can realize the excitation and measurement of multiple electrode belts during the time that one electrode belt is excited to acquire data by the conventional excitation-measurement method. Thus, the data acquisition speed is increased by multiple times, which can meet the requirements of real-time measurement of the three-dimensional electrical impedance tomography.

Example 5

In order to solve the above technical problem in the prior art, this example of the present disclosure further provides a storage medium.

A computer program for realizing the steps of the above method for measuring excitation response or realizing the steps of the above electrical impedance tomography method is stored on the storage medium of this example.

Although the embodiments disclosed in the present disclosure are as above, the contents are only embodiments adopted to facilitate the understanding of the present disclosure and are not intended to limit the present disclosure. Those skilled in the technical field of the present disclosure may make any modification and change in the form and details of the implementation without deviating from the spirit and scope of this disclosure. However, the protection scope of the present disclosure shall still be defined in the attached claims.

The invention claimed is:

1. A method for measuring excitation response, applied to an electrical impedance tomography device, wherein the electrical impedance tomography device comprises at least two electrode belts and each electrode belt comprises multiple electrodes, the at least two electrode belts being placed around a body part of a patient, the method comprising:

performing by the at least two electrode belts:

applying, at a same moment, excitation currents having different frequencies within a designated frequency range to excitation electrode pairs of the at least two electrode belts placed around the body part of the patient respectively, and measuring a voltage difference of a measurement electrode pair of each electrode belt at the moment, wherein the excitation electrode pair is selected from multiple electrodes of the same electrode belt, and the measurement electrode pair is selected from electrodes in the same electrode belt other than the excitation electrode pair;

performing discrete Fourier transform on the voltage differences of the measurement electrode pairs to obtain frequency-domain signals corresponding to the voltage differences;

sequentially taking, according to excitation frequencies of different electrode belts, a midpoint value of each two adjacent excitation frequencies as a boundary frequency of the frequency-domain signals;

separating, according to the boundary frequency, the frequency-domain signals corresponding to the voltage differences;

performing inverse discrete Fourier transform on the separated frequency-domain signals to obtain multiple sets of voltage differences respectively corresponding to the different frequencies;

using the multiple sets of voltage differences respectively corresponding to the different frequencies as electrical impedance tomography data; and reconstructing an electrical impedance image of tissue inside the body part according to the electrical impedance tomography data.

2. The method according to claim 1, wherein a quotient value obtained by dividing a difference value between an upper limit value and a lower limit value of the designated frequency range by the lower limit value does not exceed 20%.

3. The method according to claim 1, wherein the applying, at the same moment, excitation currents having different frequencies within a designated frequency range to excitation electrode pairs of the at least two electrode belts respectively, and measuring a voltage difference of a measurement electrode pair of each electrode belt at the moment, further comprises:

step one, selecting, from each electrode belt, an excitation electrode pair and a corresponding measurement electrode pair respectively;

step two, respectively applying, at the same moment, excitation currents having different frequencies within the designated frequency range to the excitation electrode pairs of all the electrode belts, and measuring voltage differences of all the measurement electrode pairs at the moment to obtain the voltage differences of all the measurement electrode pairs; and step three, selecting, from multiple electrodes of each electrode belt, a excitation electrode pair and a corresponding measurement electrode pair for multiple times according to step one, and then measuring the excitation electrode pairs and the corresponding measurement electrode pairs selected each time according to step two, until the selection of the excitation electrode pair on each electrode belt traverses all the electrodes on the electrode belt, wherein the excitation electrode pair selected each time is different from each other.

4. The method according to claim 3, wherein the step of selecting, from each electrode belt, an excitation electrode pair and a corresponding measurement electrode pair respectively, further comprises the following steps:

respectively selecting, from each electrode belt, an excitation electrode pair; and for each selected excitation electrode pair, dividing the electrodes, other than the excitation electrode pair, in multiple electrodes of the electrode belt to which the excitation electrode pair belongs, into multiple measurement electrode pairs as the corresponding measurement electrode pairs.

5. The method according to claim 4, wherein the excitation electrode pair is respectively selected from each electrode belt according to any one of an adjacent-electrode method, an opposite-electrode method and an interdigitated-electrode method.

6. The method according to claim 4, wherein, the electrodes, other than the excitation electrode pair, in multiple electrodes of the electrode belt to which the excitation electrode pair belongs, are divided into multiple measurement electrode pairs, according to any one of an adjacent-electrode method, an opposite-electrode method and an interdigitated-electrode method.

7. The method according to claim 3, further comprising the following steps:

distributing excitation electrode pairs on different electrode belts that are excited at the same moment, in up-and-down correspondence at spatial positions around an area to be measured.

8. An electrical impedance tomography method, comprising:

obtaining electrical impedance tomography data by the method for measuring excitation response according to claim 1; and reconstructing an electrical impedance image inside an area to be measured according to the electrical impedance tomography data.

9. A non-transitory computer-readable storage medium, on which a computer program is stored for realizing the method for measuring excitation response according to claim 1.

10. The non-transitory computer-readable storage medium according to claim 9, on which a computer program is further stored for realizing the steps of the electrical impedance tomography method comprising:

obtaining the electrical impedance tomography data; and reconstructing an electrical impedance image inside an area to be measured according to the electrical impedance tomography data.

11. The method according to claim 1, wherein the at least two electrode belts are distributed at equal intervals around a chest of the patient.

12. The method according to claim 1, wherein each electrode belt comprises 16 electrodes.

13. The method according to claim 1, wherein the excitation currents establish a quasi-steady state current field in the body part of the patient.

14. The method according to claim 1, wherein the at least two electrode belts comprise an upper electrode belt and a lower electrode belt, and the excitation electrode pairs on the upper electrode belt and the lower electrode belt are distributed in up-and-down correspondence at spatial positions around the body part.

15. The method according to claim 1, further comprising:

applying the reconstructed electrical impedance image for long-term monitoring of the body part of the patient.

16. The method according to claim 1, wherein the electrical impedance image is a three-dimensional electrical impedance image.

17. The method according to claim 1, wherein the voltage differences of the measurement electrode pairs are measured sequentially in a clockwise or counterclockwise direction around each electrode belt.

18. The method according to claim 1, wherein the electrical impedance tomography device simultaneously excites all of the at least two electrode belts to increase data acquisition speed compared to sequential excitation of individual electrode belts.

19. The method according to claim 1, wherein the reconstructing of the electrical impedance image is performed in real-time.

20. The method according to claim 1, wherein the multiple sets of voltage differences comprise measurement data of each electrode belt when each electrode belt is excited and measurement data of each electrode belt when other electrode belts are excited.

* * * * *